US008099268B2

(12) United States Patent
Kitching et al.

(10) Patent No.: US 8,099,268 B2
(45) Date of Patent: Jan. 17, 2012

(54) TOOTH MODELING

(75) Inventors: Ian Kitching, Saratoga, CA (US); Eric E. Kuo, Foster City, CA (US)

(73) Assignee: Align Technology, Inc., San Jose, CA (US)

(*) Notice: Subject to any disclaimer, the term of this patent is extended or adjusted under 35 U.S.C. 154(b) by 422 days.

(21) Appl. No.: 12/011,941

(22) Filed: Jan. 29, 2008

(65) Prior Publication Data

US 2008/0294405 A1 Nov. 27, 2008

Related U.S. Application Data

(63) Continuation-in-part of application No. 11/888,742, filed on Aug. 2, 2007, and a continuation-in-part of application No. 11/807,367, filed on May 25, 2007, now Pat. No. 7,878,805.

(51) Int. Cl.

*G06F 17/50* (2006.01)
*G06F 9/45* (2006.01)
*G06F 19/00* (2006.01)
*G06G 7/58* (2006.01)
*G06Q 10/00* (2006.01)
*G06Q 50/00* (2006.01)

(52) U.S. Cl. ................. 703/11; 703/1; 703/22; 705/1.1; 705/3; 700/98; 382/128

(58) Field of Classification Search ................ 703/1, 11, 703/22; 705/1.1, 3; 700/98; 382/128
See application file for complete search history.

(56) References Cited

U.S. PATENT DOCUMENTS 5,882,192 A 3/1999 Bergersen
6,394,802 B1* 5/2002 Hahn ................................ 433/37
6,632,089 B2* 10/2003 Rubbert et al. ................. 433/24
6,648,640 B2 11/2003 Rubbert et al.
6,772,026 B2* 8/2004 Bradbury et al. ............... 700/98
6,832,914 B1* 12/2004 Bonnet et al. ................. 433/213
7,245,753 B2 7/2007 Squilla et al.
7,471,821 B2 12/2008 Rubbert et al.
7,740,476 B2* 6/2010 Rubbert et al. ................. 433/24
7,826,646 B2 11/2010 Pavlovskaia et al.
2002/0015934 A1* 2/2002 Rubbert et al. ................. 433/29
2006/0063135 A1 3/2006 Mehl
2006/0204078 A1* 9/2006 Orth et al. ..................... 382/154
2007/0172291 A1* 7/2007 Yokoyama .................... 400/613
2008/0090208 A1* 4/2008 Rubbert ........................ 433/173

FOREIGN PATENT DOCUMENTS

WO WO 03/099155 A1 12/2003
WO WO 03/101330 A2 12/2003

OTHER PUBLICATIONS

"The uses of orthodontic study models in diagnosis and treatment planning". Hou, Huie-Ming, et al. Hong Kong Dental Journal 2006.*
International Search Report dated Nov. 6, 2008. (5 pgs.).

* cited by examiner

*Primary Examiner* — Paul Rodriguez
*Assistant Examiner* — Nithya Janakiraman
(74) *Attorney, Agent, or Firm* — Brooks, Cameron & Huebsch, PLLC

(57) ABSTRACT

The present disclosure includes dental appliances, devices, and methods of making and using such appliances. In one embodiment, a method for tooth modeling includes receiving a patient information file for a treatment plan patient and analyzing the patient information file to determine whether the patient is a non-adult patient.

17 Claims, 10 Drawing Sheets

710
766
768
741
746
742
780

TOOTH MODELING

RELATED APPLICATIONS

The present application is a continuation in part (CIP) of U.S. patent application Ser. No. 11/888,742, filed on Aug. 2, 2007, and is a continuation in part (CIP) of U.S. patent application Ser. No. 11/807,367 (U.S. Pat. No. 7,878,805), filed on May 25, 2007, the disclosures of which are incorporated in their entirety herein by reference.

BACKGROUND

The present disclosure is related generally to the field of dental treatment. More particularly, the present disclosure is related to a dental model system which can associate an abnormal tooth with a model tooth shape and map predefined dental references from the model shape onto the abnormal tooth to aid in accurately characterizing the tooth's positioning and/or movement.

Dental references provide feedback for dental measurements. For example, dental reference points can be used to characterize a tooth's movement, such as tipping and/or translation. Dental reference axes can be used to distinguish different directions of tooth positioning and/or movement.

Placement and/or identification of reference points can be done manually by a treatment professional or automatically through use of a computing device and executable instructions to make such identification and/or direct one or more devices to accomplish such placement. For example, the treatment professional can use a computing interface device to identify points on an image of a tooth displayed on a graphical user interface.

The treatment professional can also identify reference axes of the tooth in a similar fashion. However, manual selection of reference points and axes can yield inaccurate and inconsistent results.

As discussed above, automation of reference point selection can be performed with the assistance of a computing device. Algorithms in computing device-aided recognition of surface features can improve accuracy in some instances. For example, the maximum height of a crown can be detected by an algorithm that determines the location of cusp tips and this may improve the accuracy of reference point selection.

However, such automated systems are based on the assumption that the dental anatomy is normal. That is, the assumption that a tooth is fully intact and fully erupted.

Such automated systems rely on a set of dental features to identify reference points and axes. If a tooth is broken or partially erupted, an automated system may rely on incorrect landmarks to derive the reference points and axes.

In such situations, the automated system can incorrectly identify reference points and axes. This may result in impractical or incorrect treatment options.

Additionally, placement of an appliance over the teeth can be used to provide controlled forces in specific locations to gradually move the teeth into a new configuration. Repetition of this process with successive appliances that provide progressive repositioning may eventually move the teeth through a series of intermediate arrangements to a final desired arrangement.

In embodiments where a tooth is abnormal (a tooth that is fully formed or erupted, or abnormally formed by normal growth or accident where it is intended that this will be corrected by reconstructive means such as an inlay, onlay, cap, veneer, implant, bridge, etc) such teeth may not typically be considered in the dental treatment plan. In such embodiments, repositioning of teeth may result in inadequate space to provide for the position of an abnormal tooth and/or to provide an improved position for the abnormal tooth when the abnormal tooth becomes fully erupted or is otherwise correct or reconstructed by aligning neighboring teeth. This may lead to an abnormal tooth being crowded, misaligned, and/or moving one or more other teeth as or once the tooth is erupted.

DETAILED DESCRIPTION

Figure 1A:
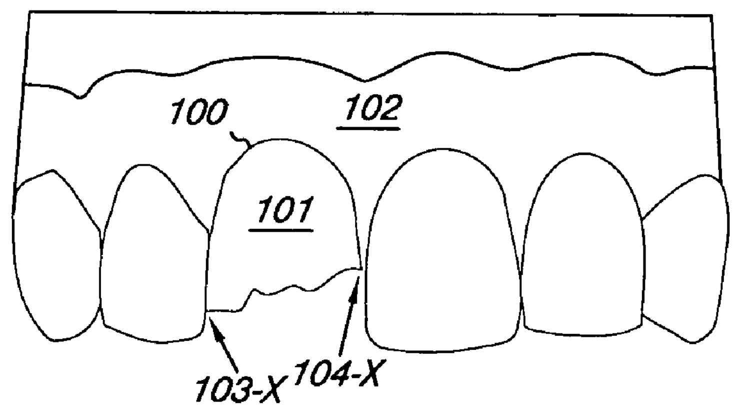
FIG. 1A illustrates an example of a broken tooth.

Embodiments of the present disclosure include computing device, system, and method embodiments for tooth modeling. In some embodiments, this modeling of teeth can use reference points to identify the location and/or movement of teeth during treatment. In various embodiments, the modeling of teeth can use virtual teeth models to aid in the formation of dental appliances for use, for example in the administration of dental treatment plans.

For instance, embodiments of the present disclosure include, a computing device readable medium having instructions for associating an abnormal tooth shape with a model tooth shape from a reference library of model tooth shapes. This can be beneficial, for example, in aiding the treatment professional with visualization of references for an abnormal tooth, among other benefits.

The present disclosure includes methods and devices for determining if a tooth or teeth are missing or partially erupted. In some embodiments, executable instructions can be provided to identify which tooth or teeth are missing or present, such as whether molars, generally, first and/or second molars, separately, canines, and/or bicuspids are present or missing.

Various embodiments may be designed to identify whether a patient is a teen patient which may indicate that the patient is more likely to have teeth missing or un-erupted. For example, in some embodiments, a computing device may have executable instructions for identifying, whether a patient is a teen patient, whether one or more teeth are missing, and/or whether one or more teeth are present.

These types of features can be provided in a parallel, serial, and/or hierarchical manner, in various embodiments. Such identification features can allow for specific teeth to be identified as present or missing which can aid in determining how to create a virtual tooth for purposes of manufacturing one or more appliances, as will be discussed below.

A model tooth shape can be based upon information from the abnormal tooth, information from a tooth in a tooth library, information about a similar tooth in the patient's mouth, or a combination of these types of information. Such information can be beneficial in the formation of one or more dental appliances for use in implementing a treatment plan, among other suitable uses.

Dental references can include those which might not be visible on an abnormal tooth due to its abnormality. For example, a chipped tooth could be missing a portion of the tooth where a dental reference is located. Associating an abnormal tooth with a model tooth shape can aid the treatment professional in visualizing missing references.

Some embodiments can include mapping a predefined dental reference from the model tooth shape onto at least a portion of the abnormal tooth shape. This can be beneficial in providing the treatment professional with more accurate and consistent references over manual selection of references based on the treatment professional's estimation, among other benefits.

Referring now to the embodiment illustrated in FIG. 1A, FIG. 1A illustrates an abnormal tooth 100 that is broken, such that a piece of the dental crown is missing. An automated system, known and used by one of ordinary skill in the art, operating on the assumption that the tooth 100 is normal, would interpret 103-X as one cusp tip while interpreting 104-X as another. FIG. 1A also displays the cementoenamel junction (CEJ) 101 and gingiva 102.

Figure 1B:
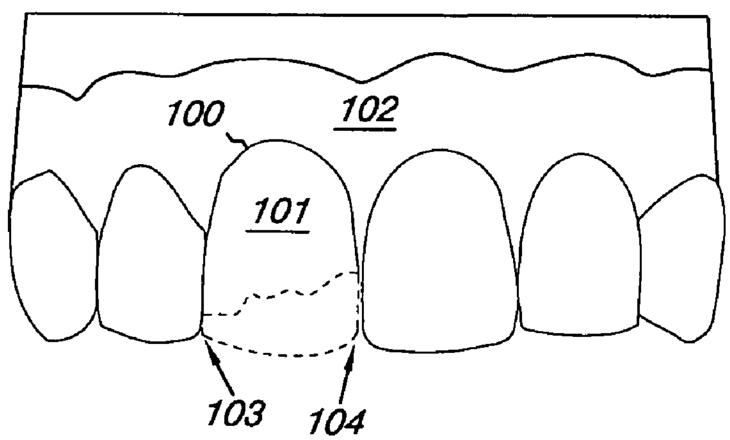
FIG. 1B illustrates the broken tooth of FIG. 1A and includes an outline of the model shape of the tooth.

FIG. 1B illustrates the broken tooth of FIG. 1A and includes an outline of what the model shape of the tooth, 100 would be, if it had not been damaged. The actual locations of the cusp tips 103 and 104 are shown.

In various embodiments, an embodiment can include adding a location of the predefined dental reference to the abnormal tooth shape based on the mapped predefined dental reference from the model tooth shape. This can aid the treatment professional when correction of the abnormal tooth involves treatment in consideration of that reference point or where an appliance is formed for the patient wherein the tooth may be repaired during treatment or where the tooth will erupt during treatment or thereafter, for example.

Embodiments can include executable instructions for mapping the predefined dental reference from the model tooth onto at least a portion of the abnormal tooth by superimposing the model tooth shape on the abnormal tooth shape. This can be beneficial in matching the model tooth shape with the actual tooth by aligning reference points.

In some embodiments, instructions can be included to create a dental image that contains at least a portion of the abnormal tooth shape and at least a portion of the model tooth shape. Such embodiments can be beneficial, for example, to aid the treatment professional in visualizing the abnormal tooth as a normal tooth.

In some embodiments, instructions can map a predefined gingival reference from the reference library corresponding to the model tooth shape onto a gingival anatomy of the abnormal tooth shape, where the dental image contains at least a portion of the abnormal tooth shape gingival anatomy and at least a portion of the model tooth shape gingival anatomy. This can be beneficial in allowing the treatment professional to visualize and accommodate changes to the gingival architecture that may occur as teeth move and erupt in accordance with orthodontic treatment and/or tooth maturation.

In various embodiments, the gingiva can be manipulated as a tooth is virtually erupted. This can be beneficial for example, so that the tooth and surrounding gingiva more accurately represent the actually condition of the tooth and gingiva at various stages during eruption of the tooth.

In some embodiments, instructions can be included for mapping the predefined dental reference from the model tooth shape onto at least a portion of the abnormal tooth shape and can include virtually mapping a portion of the predefined dental reference that does not correspond to a location on the abnormal tooth shape. Such embodiments can be beneficial, for example, in allowing the treatment professional to visualize the correct reference points and axes in order to properly characterize a tooth's movement.

In some embodiments, instructions can be executed to determine a center of rotation of the abnormal tooth shape using the location of the predefined dental references on the abnormal tooth shape based on the mapped predefined dental references from the model tooth shape.

Embodiments of the present disclosure are able to accurately identify the model locations of these reference points, for example, based on associating one or more images of model tooth shapes from the reference library with these abnormal teeth and mapping predefined dental references from the model shapes onto the abnormal tooth shapes. The locations of the CEJ 101 and gingiva 102 remain the same as in FIG. 1A.

Figure 1C:
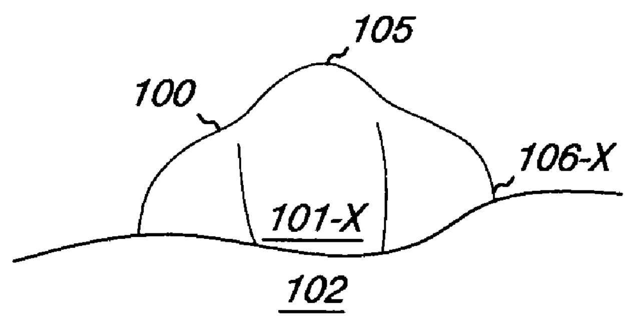
FIG. 1C illustrates an example of a partially erupted tooth.

FIG. 1C illustrates an abnormal tooth 100 that is partially erupted. This tooth includes a cusp tip 105 and gingiva 102. An automated system operating on the assumption that the tooth is normal, could incorrectly interpret 106-X as a proximal contact and 101-X as the CEJ.

Figure 1D:
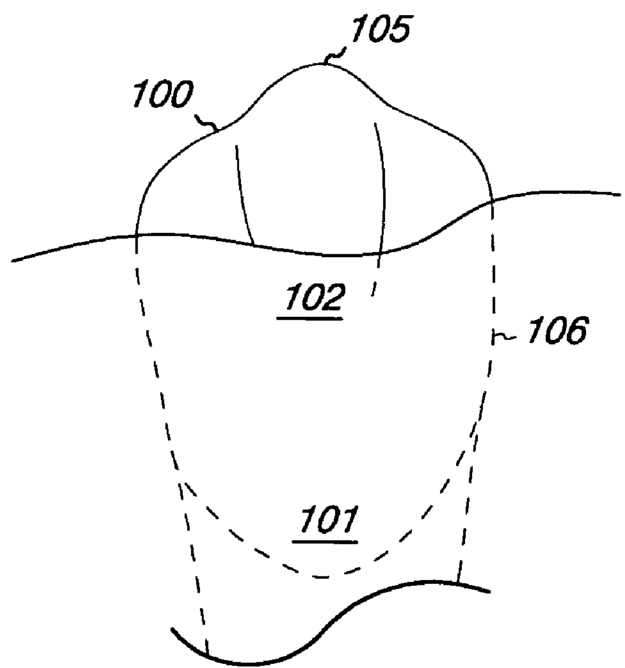
FIG. 1D illustrates the partially erupted tooth of FIG. 1C and includes an outline of a model shape of the unerupted portion of the tooth.

FIG. 1D illustrates the partially erupted tooth 100 of FIG. 1C. This tooth includes a cusp tip 105 and gingiva 102. This Figure indicates the approximate location of the proximal contact 106 and CEJ 101. Embodiments of the present disclosure can be utilized to accurately identify the model locations of these reference points, for example, based on associating one or more images of model tooth shapes from the reference library with these abnormal teeth and mapping predefined dental references from the model shapes onto the abnormal tooth shapes.

Figure 2:
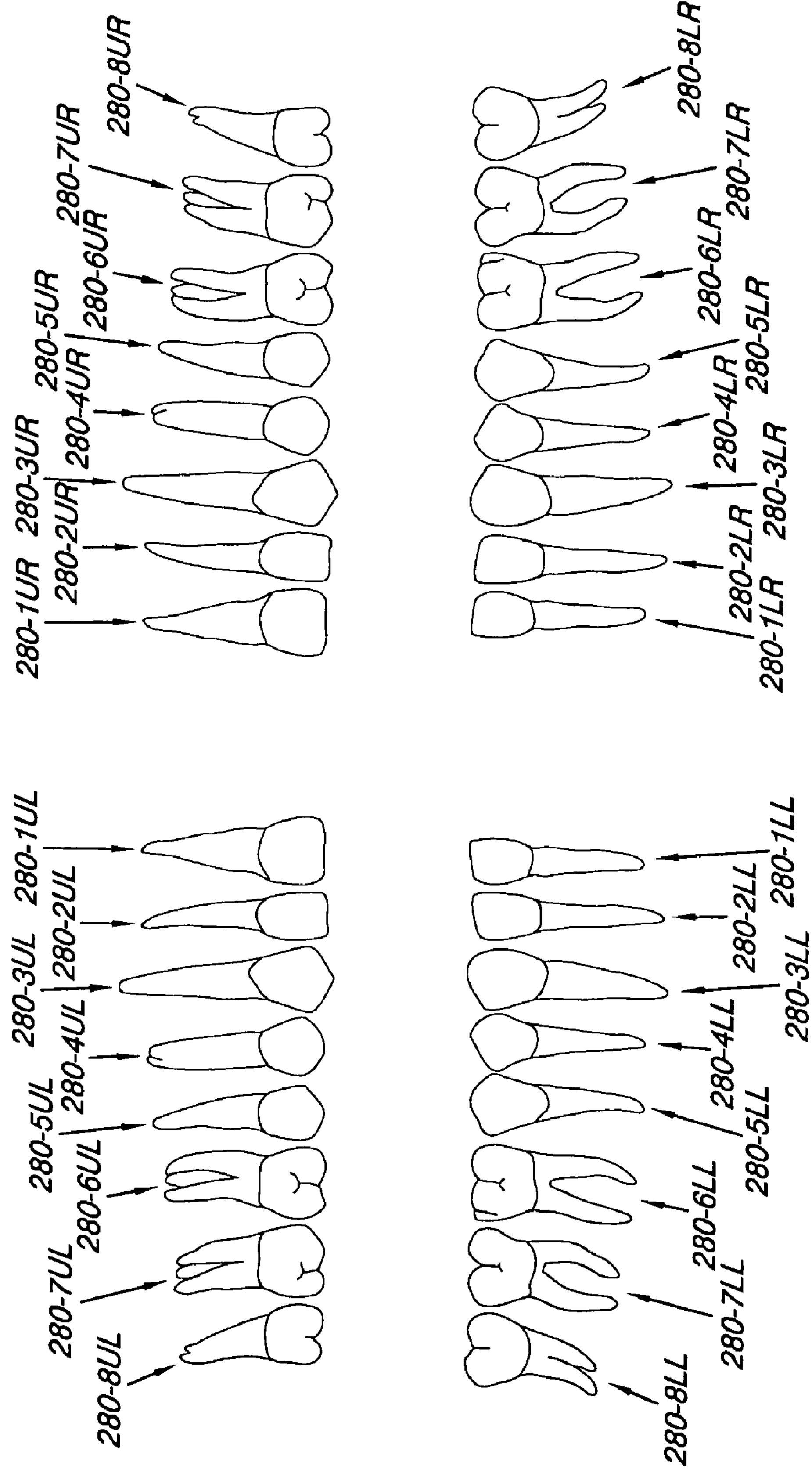
FIG. 2 illustrates a reference library of model tooth shapes.

FIG. 2 illustrates a reference library of model tooth shapes. FIG. 2 includes reference teeth for the upper right (280-1 UR, 280-2UR, 280-3UR, 280-4UR, 280-5UR, 280-6UR, 280-7UR, and 280-8UR), upper left (280-1UL, 280-2UL, 280-3UL, 280-4UL, 280-5UL, 280-6UL, 280-7UL, and 280-8UL), lower right (280-1LR, 280-2LR, 280-3LR, 280-4LR, 280-5LR, 280-6LR, 280-7LR, and 280-8LR), and lower left (280-1LL, 280-2LL, 280-3LL, 280-4LL, 280-5LL, 280-6LL, 280-7LL, and 280-8LL) groupings of teeth.

The reference library of model tooth shapes can also contain several reference points and axes for one or more teeth in the library. For instance, an example of a tooth with a plurality of reference points is illustrated in FIGS. 3A and 3B.

For instance, a theoretical root axis of a tooth may be important to accurately determine in a broken tooth, for example, if trying to assess an ideal orientation for the placement of a replacement tooth root device, such as a dental implant, using the existing broken tooth as a guide. The root axis may be more accurately determined using a superimposed ideal tooth model as opposed to using the existing broken tooth geometry as a basis for axis position determination, in some instances.

Figure 3A:
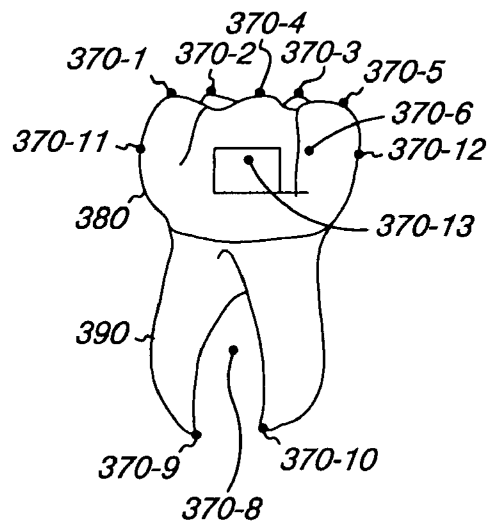
FIG. 3A illustrates a buccal view of a lower right molar selected from the reference library of model tooth shapes according to embodiments of the present disclosure.
Figure 3B:
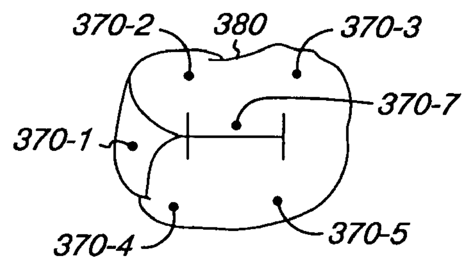
FIG. 3B illustrates an occlusal view of a lower right molar selected from the reference library of model tooth shapes according to embodiments of the present disclosure.

FIG. 3A illustrates a buccal view of a model tooth shape 380 from the reference library in FIG. 2. The tooth shape 380 illustrated in FIG. 3A is a lower right molar, for example, 280-6LR from FIG. 2. FIG. 3A also indicates the root shape 390 of the tooth shape 380.

The tooth shape in FIG. 3A is labeled with, for example, reference points (370-1, 370-2, 370-3, 370-4, 370-5, 370-6, 370-8, 370-9, 370-10, 370-11, 370-12, and 370-13) stored in the reference library. For instance, reference point 370-1 illustrates a point on the distal cusp tip.

Reference point 370-2, similarly is used to illustrate a point, on the distal lingual cusp tip, on the tooth. Reference point 370-3 illustrates a point on the mesial lingual cusp tip.

FIG. 3A, also includes reference point 370-4 that illustrates a point on the distal buccal cusp tip. Also, reference point 370-5 illustrates a point on the mesial buccal cusp tip.

Reference line 370-6 illustrates the facial aspect of clinical crown (FACC) line. Reference point 370-8 illustrates the center of resistance. Reference point 370-9 illustrates a point on the distal root tip. Reference point 370-10 illustrates a point on the mesial root tip.

Reference point 370-11 illustrates the distal contact point. Reference point 370-12 illustrates the mesial contact point. Reference point 370-13 illustrates a correct position for a virtual bracket or other dental appliance.

FIG. 3B illustrates an occlusal view of the model tooth shape 380 from the reference library in FIG. 2. The tooth shape in FIG. 3B is labeled with, for example, reference points (370-1, 370-2, 370-3, 370-4, 370-5, and 370-7).

For instance, reference point 370-1 illustrates a point on the distal cusp tip. Reference point 370-2 illustrates a point on the distal lingual cusp tip.

FIG. 3B also includes reference point 370-3 that illustrates a point on the mesial lingual cusp tip. Reference point 370-4 illustrates a point on the distal buccal cusp tip of the tooth.

Reference point 370-5 illustrates a point on the mesial buccal cusp tip. Reference line 370-7 illustrates the central groove.

Figure 3C:
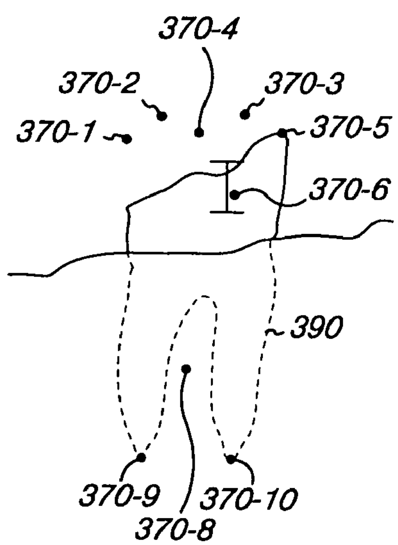
FIG. 3C illustrates reference points from a model tooth shape applied to a broken tooth according to embodiments of the present disclosure.

FIG. 3C illustrates an abnormal tooth that is broken. The tooth in FIG. 3C is a lower right molar as in FIGS. 3A and 3B. The location of the root 390 is outlined in FIG. 3C. Reference points (370-1, 370-2, 370-3, 370-4, 370-5, 370-6, 370-8, 370-9, and 370-10) from the reference library are superimposed on the tooth in the positions they would assume had the tooth not been broken, according to an embodiment of the present disclosure.

Reference point 370-1 illustrates a point on the distal cusp tip. Similarly, the reference point 370-2 illustrates a point on the distal lingual cusp tip of the tooth. Reference point 370-3 illustrates a point on the mesial lingual cusp tip.

Additionally, reference point 370-4 illustrates a point on the distal buccal cusp tip of the tooth. Reference point 370-5 illustrates a point on the mesial buccal cusp tip.

Reference line 370-6 illustrates the facial aspect of clinical crown (FACC) line. Reference point 370-8 illustrates the center of resistance. Reference point 370-9 illustrates a point on the distal root tip. Reference point 370-10 illustrates a point on the mesial root tip.

Figure 4A:
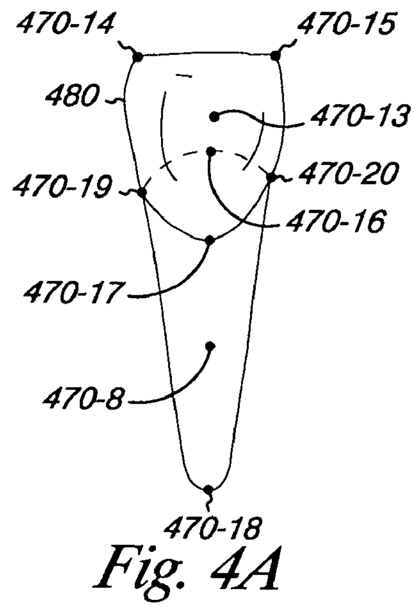
FIG. 4A illustrates a model tooth shape selected from the reference library of model tooth shapes according to embodiments of the present disclosure.

FIG. 4A illustrates a model tooth shape 480 from the reference library of FIG. 2. The tooth shape 480 illustrated in FIG. 4A is a lower incisor, for example, 280-1LR from FIG. 2.

Several reference points are labeled on the tooth. Reference point 470-8 illustrates the center of resistance of the tooth. Reference point 470-13 illustrates a correct position for a virtual bracket.

Reference points 470-14 and 470-15 illustrate points on opposite cusp tips. Reference point 470-18 illustrates a point on the root tip. Reference points 470-16, 470-17, 470-19, and 470-20 illustrate additional reference points that could be used by one of ordinary skill in the art to accurately characterize a tooth's movement using an embodiment of the present disclosure.

Figure 4B:
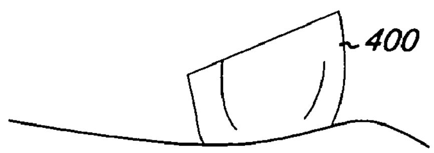
FIG. 4B illustrates an example of a broken tooth.

FIG. 4B illustrates an abnormal tooth that is broken. The tooth 400 in FIG. 4B is a lower incisor as in FIG. 4A.

Figure 4C:
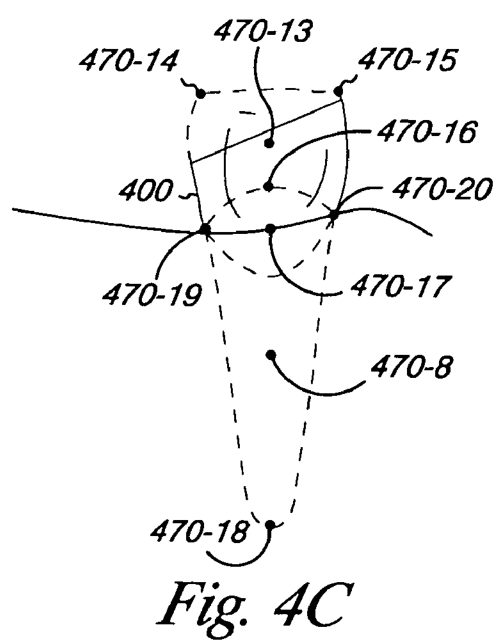
FIG. 4C illustrates reference points from a model tooth shape transferred onto an example of a broken tooth according to embodiments of the present disclosure.

FIG. 4C illustrates the model tooth shape 480 of FIG. 4A superimposed on the abnormal tooth 400 of FIG. 4B according to an embodiment described herein. The reference points described above with respect to FIG. 4A are also transferred onto the abnormal tooth 400.

Reference point 470-8 illustrates the center of resistance of the tooth. Reference point 470-13 illustrates a correct position for a virtual bracket.

Reference points 470-14 and 470-15 illustrate points on opposite cusp tips. Reference point 470-18 illustrates a point on the root tip. Reference points 470-16, 470-17, 470-19, and 470-20 illustrate additional reference points that could be used by one of ordinary skill in the art to accurately characterize a tooth's movement using an embodiment of the present disclosure.

In some embodiments, the computing device superimposes the model tooth shape on the abnormal tooth shape by a shrink-wrap sizing algorithm. This is illustrated in FIGS. 5A-5C.

Figure 5A:
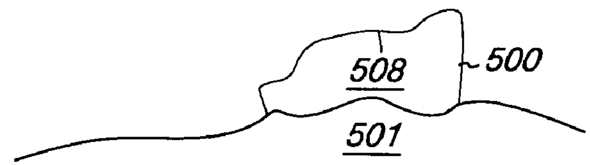
FIG. 5A illustrates an example of a broken tooth.

For example, FIG. 5A illustrates an abnormal tooth that is broken. Tooth 500 is a lower molar. FIG. 5A also illustrates the CEJ at 501. The crown of the tooth 500 is provided at 508.

Figure 5B:
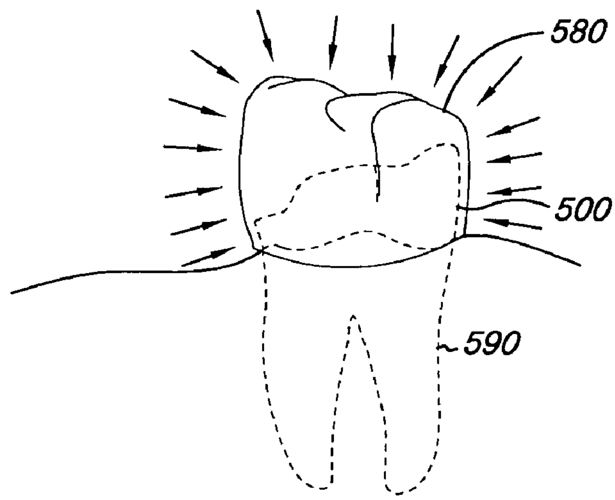
FIG. 5B illustrates the operation of a shrink-wrap algorithm matching a model tooth shape from the reference library to the broken tooth of FIG. 5A according to embodiments of the present disclosure.
Figure 5C:
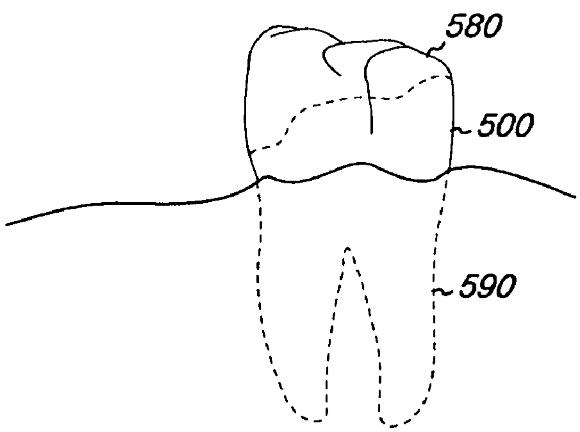
FIG. 5C illustrates the image of the model tooth shape superimposed on the broken tooth after operation of the shrink-wrap algorithm according to embodiments of the present disclosure.

FIG. 5B illustrates a model tooth shape 580 superimposed over the broken tooth 500 from FIG. 5A. The root of the model tooth shape 580 is illustrated at 590.

The arrows indicate that the model tooth shape 580 is being shrink-wrapped according to an embodiment described herein. The shrink-wrap operation can, for example, utilize executable instructions to scale the size of the model tooth shape 580 down so that one or more of its reference points correspond to one or more reference points of the abnormal tooth 500.

FIG. 5C illustrates the model tooth shape 580 from FIG. 5B after it has been reduced by the shrink-wrap operation according to an embodiment described herein. In FIG. 5C, the model tooth shape 580 is collinear with the outer, normal surfaces of the abnormal tooth 500.

The outer, normal surfaces of abnormal tooth 500 are those outer surfaces, which would be continue to be outer surfaces if the abnormal tooth 500 were unbroken and fully erupted. An outline of the root 590 may also be provided to aid in the fit in some embodiments.

In some embodiments, the portion of the tooth to be modeled may be below, at, or transiting the gingiva adjacent to the tooth. In such embodiments, executable instructions can be utilized in the mapping of a predefined dental reference from a model tooth shape onto at least a portion of the abnormal tooth shape where the mapping includes virtually mapping a portion of the predefined dental reference that is at least partially obscured by the gingiva.

Figure 6:
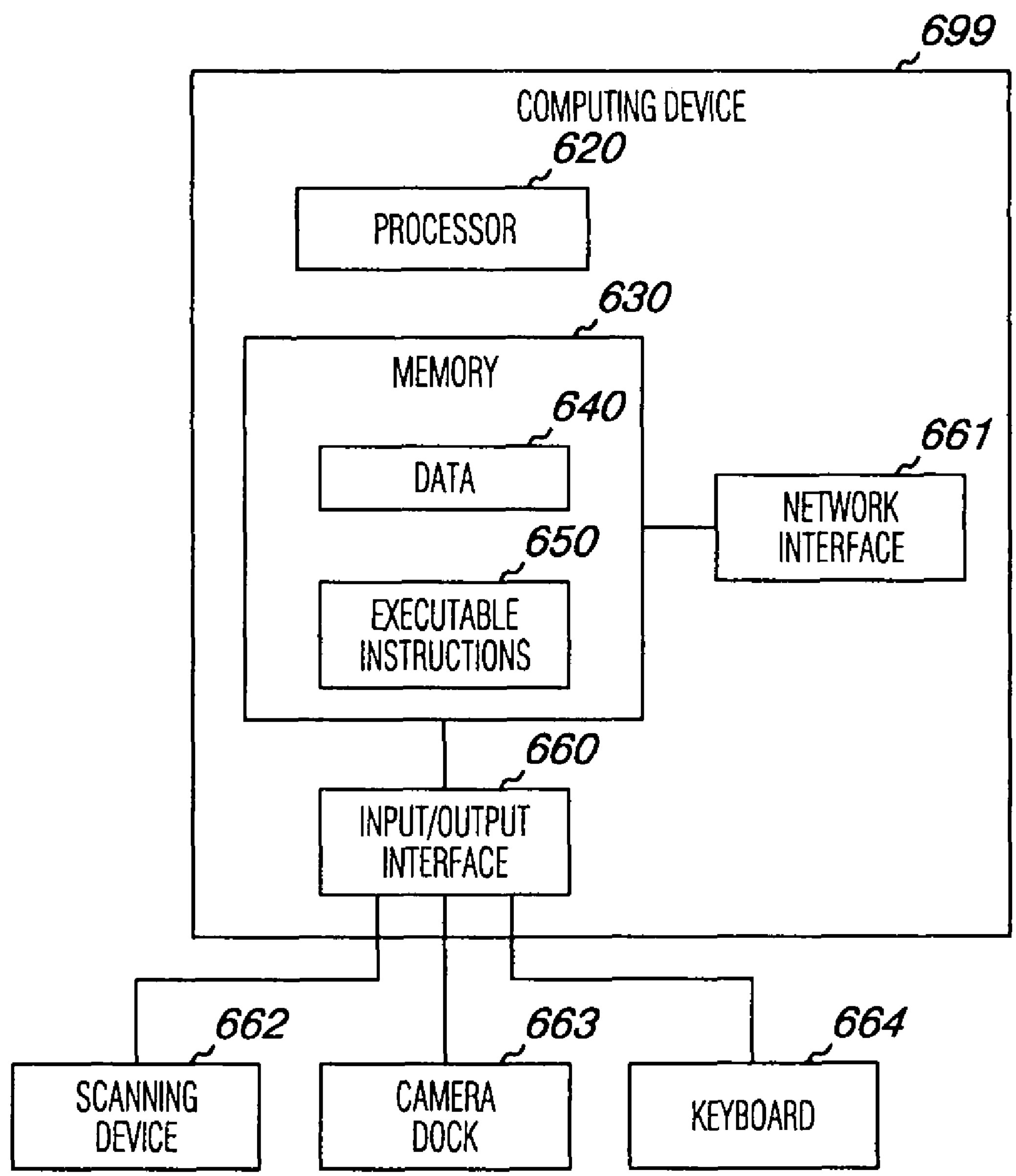
FIG. 6 provides a system for analyzing various physical teeth and associating an abnormal tooth shape with a model tooth shape and mapping predefined dental references from the model shape onto the abnormal tooth according to embodiments of the present disclosure.

FIG. 6 provides a system for analyzing the positions of various physical teeth and in creating virtual models thereof that can be used with embodiments of the present disclosure. In the system illustrated in FIG. 6, the system includes a computing device 699 having a processor 620 and memory 630. The memory can include various types of information including data 640 and executable instructions 650 as discussed herein.

Additionally, as illustrated in the embodiment of FIG. 6, a system can include a network interface 661. Such an interface can allow for processing on another networked computing device or such devices can be used to obtain information about the patient or executable instructions for use with various embodiments provided herein.

As illustrated in the embodiment of FIG. 6, a system can include one or more input and/or output interfaces 660. Such interfaces can be used to connect the computing device with one or more input or output devices. For example, in the embodiment illustrated in FIG. 6, the system includes connectivity to a scanning device 662, a camera dock 663, and a keyboard 664.

Such connectivity can allow for the input and/or output of image information (e.g., scanned images or digital pictures, etc.) or instructions (e.g., input via keyboard) among other types of information. Although some embodiments may be distributed among various computing devices within one or more networks, such systems as illustrated in FIG. 6 can be beneficial in allowing for the capture, calculation, and analysis of the various information discussed herein.

As discussed above, embodiments of the present disclosure also include a number of method embodiments. For example, in some embodiments, a method can include creating a reference library including a set of model tooth shapes with model tooth geometries, where each model tooth shape has a predefined dental reference.

Some embodiments include associating an abnormal tooth shape with a model tooth shape from the reference library. This can be beneficial in aiding the treatment professional with visualization of references for an abnormal tooth.

As discussed above, such embodiments can include references which might not be visible on an abnormal tooth due to its abnormality. For example, a chipped tooth could be missing a portion of the tooth where a dental reference is located.

Embodiments can include superimposing the model tooth shape on the abnormal tooth shape. This can be beneficial in allowing the treatment professional to visualize the shape and references from a model tooth shape superimposed on the abnormal tooth shape representing a tooth possibly requiring treatment.

Such computing devices and systems can include executable instructions that can be executed to virtually erupt teeth that are unerupted or partially erupted. Such devices and systems can be useful in seeing the changes in the teeth and gingiva around the teeth that are erupting and can be used in designing dental appliances, such as aligners (e.g., the aligner of FIG. 7).

The virtual eruption can be based on a number of informational resources for providing the movement of the tooth and/or gingiva being erupted and/or moved. For example, information can be provided based upon information from the abnormal tooth (e.g., mapping of references), information from a tooth in a tooth library, information about a similar tooth in the patient's mouth, information about the general movements of a tooth or teeth and/or gingiva during such processes, or a combination of these types of information.

Various embodiments can include mapping the predefined dental reference from the model tooth shape onto at least a portion of the abnormal tooth shape. This can be beneficial in providing the treatment professional with more accurate and consistent references over manual selection of references based on the treatment professional's estimation.

Some embodiments include adding a location of the predefined dental reference to the abnormal tooth shape based on the mapped predefined dental reference from the model tooth shape. This can aid the treatment professional when correction of the abnormal tooth involves treatment in consideration of that reference point.

Embodiments can include superimposing the model tooth shape on the abnormal tooth shape by a best-fit algorithm. This can be beneficial in further automating the process of matching reference points from a model tooth shape with an abnormal tooth shape.

In some embodiments, for example, each model tooth shape can have at least six predefined dental references. The one or more reference points can be individual points, lines, shapes, or other markers that can be used to determine an object's position in space. This can be beneficial in allowing a treatment professional to have enough information to accurately characterize a tooth's movement.

In some embodiments, the predefined dental references can include virtual orthodontic brackets (e.g., 370-13 in FIG. 3A). Virtual orthodontic brackets on a plurality of teeth in a jaw, for example, can be lined up using a virtual wire.

In so doing, a prescription can be built into the virtual bracket for inclination, angulation, rotation, and/or in-out, for example, based on the modeled teeth templates. The modeled teeth templates can be custom adjusted to fit the actual teeth using a best fit algorithm, such as that described above.

As discussed with respect to FIG. 6, embodiments of the present disclosure also include a computing device including a processor, memory connected to the processor, and computing device executable instructions storable in the memory and executable by the processor. For example, in some embodiments, the device can associate an abnormal tooth shape with a model tooth shape from a reference library of model tooth shapes, map a predefined dental reference from the model tooth shape onto at least a portion of the abnormal tooth shape, and add a location of the predefined dental references to the abnormal tooth based on the mapped predefined dental references from the model tooth.

Such functions can be provided by executable instructions stored in memory and executable by a logic circuit such as a processor. The library files and/or related tooth shape information can also be stored in memory.

In some embodiments, the memory of the computing device includes the reference library including a set of model tooth shapes with model tooth geometries, where each model tooth shape includes the predefined dental references. The model tooth shapes and predefined dental references can be utilized by the device to allow a treatment professional to accurately characterize a tooth's movement as discussed above.

In some embodiments, the computing device can include executable instructions to create a dental image of the abnormal tooth shape, where abnormalities of the abnormal tooth shape are virtually corrected by the superimposed model tooth shape. This can be beneficial in allowing the treatment professional to accurately characterize a tooth's movement based on accurate and correct dental references as discussed above.

Figure 7:
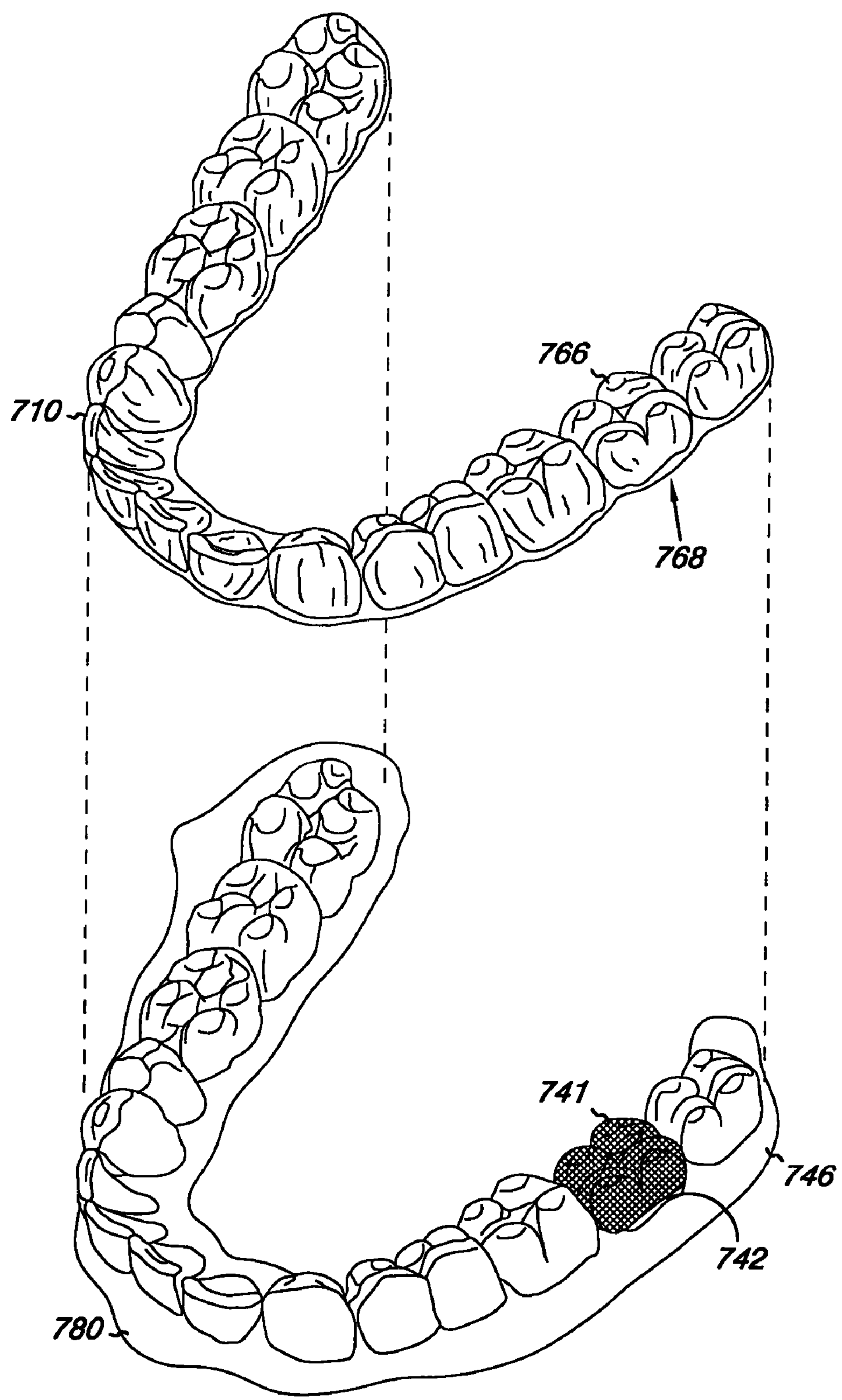
FIG. 7 illustrates an appliance being applied to a set of teeth that has been prepared according to embodiments of the present disclosure.

FIG. 7 illustrates a position adjustment appliance 710 that can be fitted over a set of teeth 780. Appliances according to the present disclosure include a plurality of incremental position adjustment appliances. The appliances, such as appliance 710 illustrated in FIG. 7, can be utilized to affect incremental repositioning of individual teeth in the jaw 780 as described generally above, among other suitable uses.

The methods of the present disclosure can employ any positioners, retainers, and/or other removable appliances for finishing and maintaining teeth positions in connection with a dental treatment. These appliances may be utilized by the dental professional in performing his treatment plan that was created using some of the methods described herein.

In some embodiments, instructions can be executed to create a dental treatment plan based on the location of the predefined dental references on the abnormal tooth shape. Such an embodiment may also include creating a predefined set of appliances for placement over one or more teeth.

An appliance (e.g., appliance 710 in FIG. 7) can, for example, be fabricated from a polymeric shell, or formed from other material, having a cavity shaped to receive and apply force to reposition one or more teeth from one teeth arrangement to a successive teeth arrangement. The shell may be designed to fit over a number of, in many instances all teeth, present in the upper or lower jaw 780.

In some embodiments, such as that illustrated in FIG. 7, a dental appliance 710 can include a number of tooth apertures for the placement of teeth 766 therein and one or more spaces 768 formed by analysis of information about a patient's mouth and wherein the space represents a position of a fully erupted virtual tooth 741 representing a tooth that has not fully erupted 742 and wherein an appliance space portion 768 is oriented to be received over the position of the tooth that has not fully erupted in the mouth of the patient. Such a space portion can be beneficial, for example, in forming an appliance that can accommodate the tooth as it is erupting or as it will be reconstructed and in forming the appliance so that the gingival line of the appliance is close to that of the gingiva line of the erupting or reconstructed tooth.

Such embodiments can be accomplished, for example, by using a computing device with executable instructions therein (e.g., computing device 699 of FIG. 6) to provide a virtual model of the teeth with the one or more unerupted teeth shown in the virtual model as fully erupted. In this manner, the space can be reserved for the eruption of the tooth and the other teeth can be manipulated with the reservation of this space in mind. This virtual model can then be used in the process of forming one or more dental appliances.

In some embodiments, a virtual erupted tooth can be superimposed over a virtual unerupted or partially erupted tooth on a display that shows the virtual model. Some embodiments can illustrate a virtual tooth being erupted (i.e., erupting from an unerupted or partially erupted condition to a fully erupted condition).

Accordingly, in some embodiments, where several appliances are created for the movement of teeth over time, the appliance space portion can be created to increase or change the size of the space portion from one appliance to the next subsequent appliance as the teeth are move to accommodate the erupting tooth. For example, where initially there may not be enough room for an unerupted or partially erupted tooth to erupt, the various appliances can be designed through use of the virtual model to create such space based upon the use of a virtual erupted tooth being illustrated for a virtual unerupted tooth in the virtual model.

In various embodiments, the virtual erupted tooth can replace the virtual unerupted or partially erupted tooth on the display. In some embodiments, the virtual erupted and unerupted/partially erupted teeth images can be interchanged, or switched, through initiation by a user of the computing device, for example.

In various embodiments, the gingiva (e.g., gingiva 746) can be manipulated as a tooth (e.g., 741) is virtually erupted. This can be beneficial for example, so that the tooth and surrounding gingiva more accurately represent the actually condition of the tooth and gingiva at various stages during eruption of the tooth.

In some embodiments, the dental appliance can be formed such that the appliance space portion includes a surface that is shaped to mate with a second appliance surface to be positioned adjacent to the surface of the space. For example, when an appliance for the lower jaw includes an appliance space portion, the top surface of the appliance space portion can be shaped to mate with the bottom surface of an appliance to be used on the upper jaw of the patient. In this way, although the tooth or teeth are not fully erupted, the aligners will fit as though they are fully erupted.

Further, in some embodiments, the appliance can be fitted with a pontic. Such embodiments may lessen the visibility of the space created in the appliance for the erupting tooth.

In some embodiments, a tab can be formed in the appliance over a position of an unerupted or partially erupted tooth. Such a concept is discussed in U.S. patent application Ser. No. 11/807,367.

Figure 8:
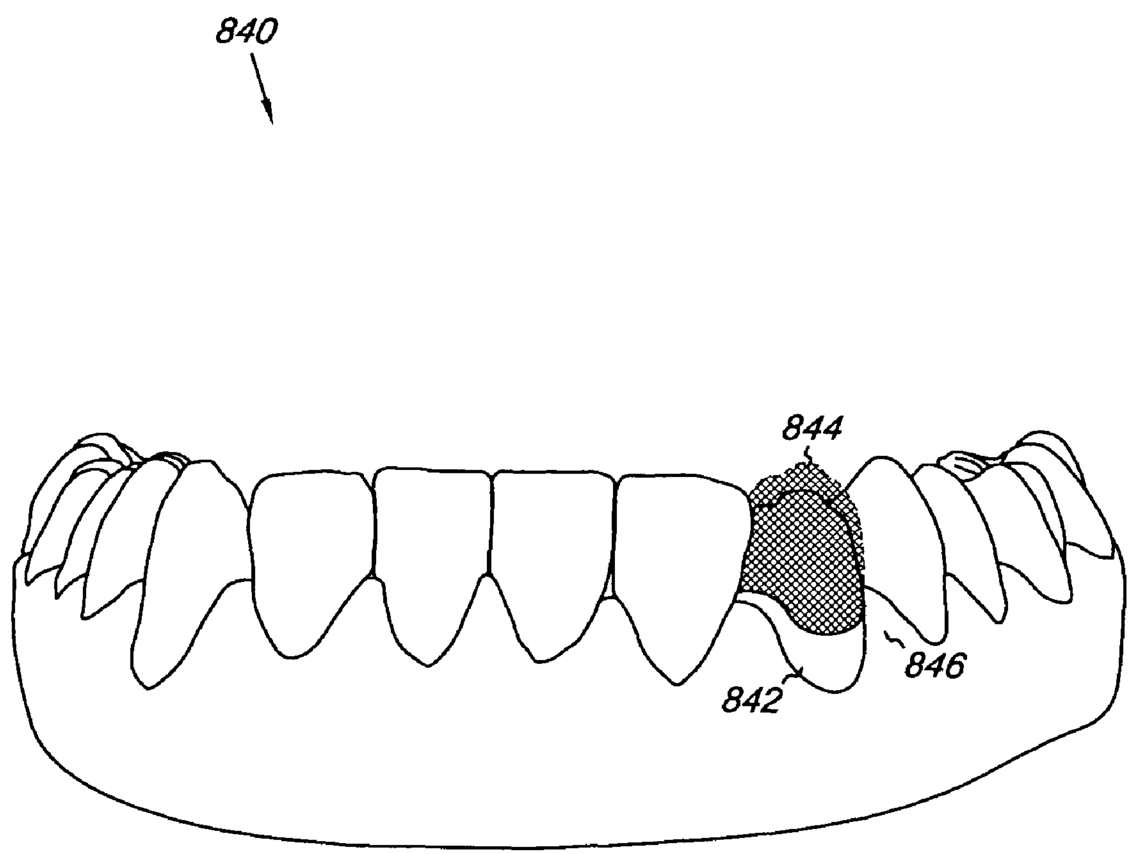
FIG. 8 illustrates a representation of a partially erupted canine tooth and a fully erupted canine tooth according to an embodiment of the present disclosure.

FIG. 8 illustrates a representation of a partially erupted canine tooth and a fully erupted canine tooth according to an embodiment of the present disclosure. As illustrated in FIG. 8, a computing device can be provided with executable instructions such that more than one tooth condition can be presented within a virtual model. For example, in various embodiments, the tooth conditions can be masked, shaded, and/or switched, among other functions capable of allowing usage of multiple tooth conditions.

In some such embodiments, one of the two conditions of the tooth can be masked so that it cannot be seen. In various embodiments, such as that illustrated in FIG. 8, a tooth condition may be shaded so that both tooth conditions can be viewed at the same time. Although discussed here with two conditions, in some embodiments, there may be more than two and one or more of the conditions may be masked and/or shaded, in some such embodiments.

In various embodiments, executable instructions may be used to provide a user the ability to turn the masking on or off and/or to switch a view on a computing device display or other display from a first tooth condition (e.g., un-erupted) to one or more subsequent tooth conditions (e.g., erupted). This may allow a treatment professional and/or a manufacturing employee to review the proposed virtual design before, during, or after manufacture or one or more appliances based upon the one or more virtual models created. In some embodiments, executable instructions may be provided to enable such users to alter the virtual model based upon their analysis of the displayed model.

In the embodiment illustrated in FIG. 8, the virtual model 840 includes a partially erupted tooth condition 842 and an erupted tooth condition 844. Also illustrated is a gingival area 846 that can be modified as discussed herein.

In some embodiments, one or more gingival conditions can be provided. In some such embodiments, the gingival conditions can be provided similarly to that of the tooth conditions (e.g., masking, shading, switching, etc.)

Figure 9:
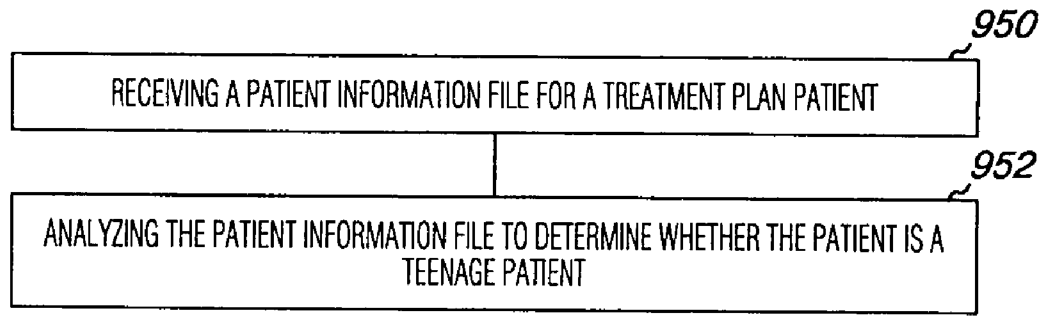
FIG. 9 illustrates a method for providing tooth modeling according to an embodiment of the present disclosure.

FIG. 9 illustrates a method for providing tooth modeling according to an embodiment of the present disclosure. At block 950, the embodiment of FIG. 9 includes receiving a patient information file for a treatment plan patient. In some embodiments, the method can include analyzing the patient information file to identify if one or more of a patient's teeth are missing.

The embodiment of FIG. 9 includes analyzing the patient information file to determine whether the patient is a non-adult patient (i.e., at an age in which it is likely or possible that not all teeth will have fully erupted), at block 952. In various embodiments, determining whether the patient is a non-adult patient is accomplished by determining a status of a flag provided in the patient information file. In some embodiments, a flag can be used to indicate if a tooth, or one or more particular teeth are missing or present, regardless of a patient's age.

A flag can be any type of indicator, such as a computing device readable indicator like a bit in a database or program, among other indicator types. For instance, a flag can be provided in a title or other portion of a patient information file. In such a manner, the flag may take up little or no additional memory in or associated with a computing device.

In some embodiments a method may include analyzing the patient information file to identify if one or more particular teeth are present. For example, the patient information file may be reviewed to see if any data for a particular tooth, teeth or tooth type, is present.

For instance, the patient information file can be reviewed to see if any second molar data is present representing one or more of a patient's second molars. If the second molars are all present (e.g., two second molars for a single arch and four second molars for two arches).

In such instances, if a second molar is missing, the tooth modeling device can create a second molar for use in the virtual model that will be utilized in fabricating the tab that is to be used for that tooth. This can, for example, be accomplished by accessing a library of sample teeth and finding a suitable sample to be used, by copying another of the patient's teeth to create the tooth to be used in the virtual model (e.g., another second molar or a first molar), by using information about the missing tooth, or a combination of these types of information.

In some embodiments, the size of the space available between teeth and/or other mouth features may be used to aid in the shaping and/or scaling of the tooth sample to be selected and/or shaped to be used in the virtual model. In some embodiments, one or more characteristics of one or more of the patient's other teeth may be used to aid in the shaping and/or scaling of the tooth sample to be selected and/or shaped to be used in the virtual model.

In some embodiments, a method can include copying information about a particular tooth that is present and inserting at least a portion of the information into a place within the file used to reference a missing tooth. In some embodiments, this information can be modified (e.g., shaped and/or scaled) to better fit the tooth information to the particular space to which the virtual tooth is to be positioned.

In this manner, the copied information about a particular tooth that is present may be manipulated to estimate what a missing tooth may look like. In such embodiments, the manipulated information can be inserted into a place within the file used to reference a missing tooth.

As indicated above, in some embodiments, information about a particular tooth can be obtained from a database of ideal teeth. Such information can, for example, be utilized to estimate what a missing tooth may look like, as discussed above. In some embodiments, this information can be used with information about the missing tooth to estimate what a missing tooth may look like.

Figure 10:
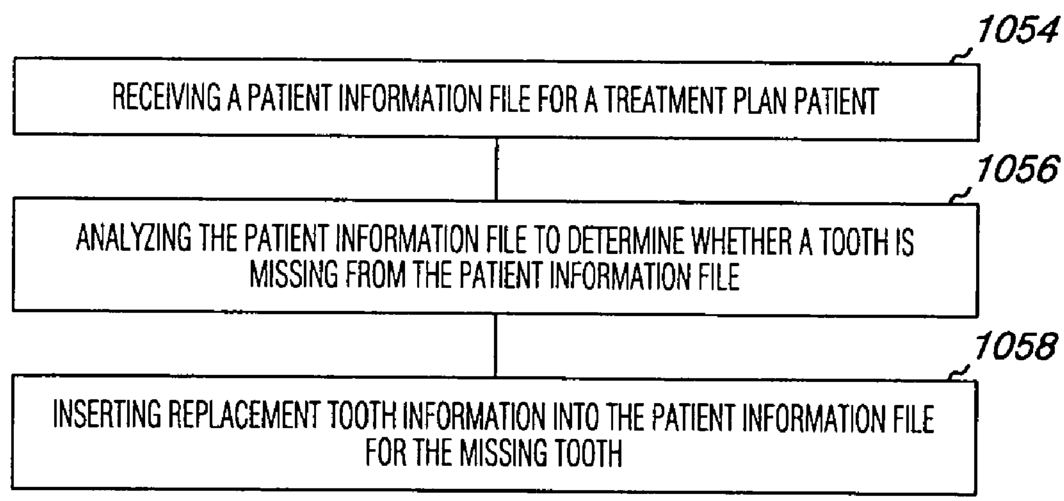
FIG. 10 illustrates another method for providing tooth modeling according to an embodiment of the present disclosure.

FIG. 10 illustrates another method for providing tooth modeling according to an embodiment of the present disclosure. At block 1054, the embodiment of FIG. 10 includes receiving a patient information file for a treatment plan patient.

The embodiment of FIG. 10 includes analyzing the patient information file to determine whether a tooth is missing from the patient information file, at block 1056. This can be accomplished, for example, by reviewing one or more positions within the patient information file where information about a particular tooth is supposed to be.

For instance, in some embodiments, the file can be a database or other file type that may have specific positions defined for such information. In some embodiments, the information file may have a flag indicating that a tooth is missing or present.

In the embodiment of FIG. 10, at block 1058, the method includes inserting replacement tooth information into the patient information file for the missing tooth. The replacement tooth information, as discussed above, can be obtained in various manners.

For example, the replacement tooth information can be obtained from a database of ideal/model teeth. In some embodiments, the replacement tooth information can be obtained from a particular tooth (e.g., tooth data) in a patient information file. In various embodiments, the replacement tooth information can be obtained from an estimated tooth shape based upon information obtained from a database of ideal teeth and/or from one or more particular teeth in the patient information file, as indicated above.

In some embodiments, it may be useful to also have the shape of the gingiva around at least a portion of the tooth or teeth, that are being virtually created or erupted, be modified. In this manner, when a tooth is virtually erupted when it is actually not erupted in the patient's mouth, the virtual model created is more likely to be accurate, in some instances, since the gingiva during an actual eruption of a tooth is altered from its un-erupted state. Accordingly, such information can be utilized in the formation of one or more dental appliances.

In some embodiments, gingiva information, for example, can be obtained from a database (e.g., a library) of ideal gingiva shapes, can be obtained for analysis of other gingiva points within the mouth of the patient or a combination of information resources. In various embodiments, the gingiva information can be obtained from gingiva surrounding a particular tooth in the patient information file.

The gingiva can, for example, be from the area where the tooth is to be added, from a neighboring tooth, from a tooth of a similar type (e.g., a molar or second molar) or other such areas of the patient's mouth. In some embodiments, gingiva information can be obtained from an estimated gingiva shape based upon information obtained from a database of ideal gingiva shapes and gingiva surrounding one or more particular teeth in the patient information file. In this manner actual patient information can be used with ideal gingiva and/or tooth information to provide a tooth/gingival model.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the use of the terms “a”, “an”, “one or more”, “a number of”, or “at least one” are all to be interpreted as meaning one or more of an item is present. Additionally, it is to be understood that the above description has been made in an illustrative fashion, and not a restrictive one. Combination of the above embodiments, and other embodiments not specifically described herein will be apparent to those of skill in the art upon reviewing the above description.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in a single embodiment for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed:

1. A non-transitory computer readable medium having instructions for causing a device to perform a method for tooth modeling, comprising:

receiving a patient information file for a treatment plan patient;

analyzing the patient information file to determine whether a tooth is missing from the patient information file; and displaying a first tooth condition and a second tooth condition within a virtual model, wherein the first tooth condition is an un-erupted tooth and the second tooth condition is the un-erupted tooth virtually erupted and wherein the virtual model allows both conditions to be viewed at the same time.

2. The medium of claim 1, wherein the method includes determining whether a patient is a non-adult patient by determining a status of a flag provided in the patient information file.

3. The medium of claim 1, wherein determining whether the patient is a non-adult patient is accomplished by determining a status of a flag provided in a title of the patient information file.

4. The medium of claim 1, wherein the method includes analyzing the patient information file to identify if one or more particular teeth are present.

5. The medium of claim 1, wherein the method includes copying information about a particular tooth that is present and inserting at least a portion of the information into a place within the file used to reference the missing tooth.

6. The medium of claim 5, wherein the method includes copying information about a particular tooth that is present and manipulating the copied information to estimate what the missing tooth may look like.

7. The medium of claim 6, wherein the method includes virtually erupting a tooth on a display based upon the estimate of what the missing tooth may look like.

8. The medium of claim 5, wherein the method includes inserting the manipulated information into a place within the file used to reference a missing tooth.

9. The medium of claim 5, wherein the method includes obtaining information about a particular tooth in a database of ideal teeth and utilizing the obtained information to estimate what the missing tooth may look like.

10. The medium of claim 5, wherein the method includes obtaining information about a particular tooth in a database of ideal teeth and utilizing the obtained information and information about the missing tooth to estimate what the missing tooth may look like.

11. A tooth modeling device, comprising:

a processor; and memory having device executable instructions executable by the processor to:

receive a patient information file for a treatment plan patient; and analyze the patient information file to determine whether a tooth is missing from the patient information file; and display a first tooth condition and a second tooth condition within a virtual model, wherein the first tooth condition is an un-erupted tooth and the second tooth condition is the un-erupted tooth virtually erupted and wherein the virtual model allows both conditions to be viewed at the same time.

12. The tooth modeling device of claim 11, wherein the first tooth condition and second tooth condition are selected from the group of conditions including switched, masked, and shaded.

13. A tooth modeling device, comprising:

a processor; and memory having device executable instructions executable by the processor to:

receive a patient information file for a treatment plan patient; and analyze the patient information file to determine whether a tooth is missing from the patient information file; and display a first gingiva condition and a second gingiva condition within a virtual model, wherein the first gingiva condition is a gingiva of an un-erupted tooth and the second gingiva condition is a gingiva of the un-erupted tooth virtually erupted and wherein the virtual model allows both conditions to be viewed at the same time.

14. A non-transitory computer readable medium having instructions for causing a device to perform a method for tooth modeling, comprising:

receiving a patient information file for a treatment plan patient; and analyzing the patient information file to determine whether a tooth is missing from the patient information file; and displaying a first gingiva condition and a second gingiva condition within a virtual model, wherein the first gingiva condition is a gingiva of an un-erupted tooth and the second gingiva condition is a gingiva of the un-erupted tooth virtually erupted and wherein the virtual model allows both conditions to be viewed at the same time.

15. The medium of claim 14, wherein gingiva information is obtained from a database of ideal gingiva shapes.

16. The medium of claim 14, wherein gingiva information is obtained from gingiva surrounding a particular tooth in the patient information file.

17. The device of claim 14, wherein gingiva information is obtained from an estimated gingiva shape based upon information obtained from a database of ideal gingiva shapes and gingiva surrounding one or more particular teeth in the patient information file.

* * * * *